US00PP11817P2

(12) United States Plant Patent
Fuess

(10) Patent No.: US PP11,817 P2
(45) Date of Patent: Mar. 13, 2001

(54) CHRYSANTHEMUM PLANT NAMED 'EMPIRE RIVIERA'

(76) Inventor: Janet S. Fuess, 22 Country Club Dr., New York Mills, NY (US) 13417

( * ) Notice: Subject to any disclaimer, the term of this patent is extended or adjusted under 35 U.S.C. 154(b) by 0 days.

(21) Appl. No.: 09/224,734

(22) Filed: Jan. 4, 1999

(51) Int. Cl.[7] ..... A01H 5/00
(52) U.S. Cl. ..... Plt./286

(58) Field of Search ..... Plt./286, 297

*Primary Examiner*—Howard J. Locker
(74) *Attorney, Agent, or Firm*—C. A. Whealy

(57) ABSTRACT

A distinct cultivar of Chrysanthemum plant named 'Empire Riviera', characterized by its uniformly mounded and relatively compact plant habit; uniform flowering; daisy-type inflorescences that are about 4.1 cm in diameter; attractive rose pink ray florets and bright yellow disc florets; and numerous inflorescences per plant.

1 Drawing Sheet

BACKGROUND OF THE INVENTION

The present invention relates to a new and distinct cultivar of Chrysanthemum plant, botanically known as *Dendranthema grandiflora* and referred to by the cultivar name Empire Riviera.

The new cultivar is a product of a planned breeding program conducted by the Inventor in New York Mills, N.Y. The objective of the breeding program is to create new garden-type Chrysanthemum cultivars having inflorescences with desirable inflorescence forms and floret colors and good garden performance.

The new cultivar originated from a cross made by the Inventor in October, 1993 of two unidentified proprietary seedling selections.

The cultivar Empire Riviera was discovered and selected by the Inventor as a flowering plant within the progeny of the stated cross in a controlled environment in New York Mills, N.Y., in September, 1994. The selection of this plant was based on its desirable inflorescence form and ray floret color.

Asexual reproduction of the new cultivar by terminal cuttings taken in a controlled environment in New York Mills, N.Y., has shown that the unique features of this new Chrysanthemum are stable and reproduced true to type in successive generations.

SUMMARY OF THE INVENTION

The cultivar Empire Riviera has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Empire Riviera'. The characteristics in combination distinguish 'Empire Riviera' as a new and distinct cultivar:

1. Uniformly mounded and relatively compact plant habit.
2. Uniform flowering.
3. Daisy-type inflorescences that are about 4.1 cm in diameter.

4. Attractive rose pink ray florets and bright yellow disc florets.
5. Numerous inflorescences per plant.

The new Chrysanthemum is similar to the Chrysanthemum cultivar Kimberly (disclosed in U.S. Plant Pat. No. 9,026). However in side-by-side comparisons under commercial practice, plants of the new Chrysanthemum differed from plants of the cultivar Kimberly in the following characteristics:

1. Plants of the new Chrysanthemum flower about five days earlier than plants of the cultivar Kimberly.
2. Plants of the new Chrysanthemum have more ray florets per inflorescence than plants of the cultivar Kimberly.
3. Ray florets of plants of the new Chrysanthemum are darker in color than ray florets of plants of the cultivar Kimberly.

BRIEF DESCRIPTION OF THE PHOTOGRAPHS

The accompanying photographs illustrate the overall appearance of the new cultivar.

The photograph at the top of the sheet comprises a side perspective view of a typical flowering plant of 'Empire Riviera'.

The photograph at the bottom of the sheet comprises a close-up view of typical inflorescences of the cultivar 'Empire Riviera'. These photographs show the colors as true as it is reasonably possible to obtain in colored reproductions of this type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Leamington, Ontario, Canada, under conditions which approximate those generally used in commercial garden Chrysanthemum production. One rooted cutting was planted in a 15-cm container on July 20, 1998 and plants were grown outdoors under natural season conditions. Measurements and numerical values represent averages for typical flowering containers.

Botanical classification: *Dendranthema grandiflora* cultivar Empire Riviera.

Commercial classification: Daisy-type garden chrysanthemum.

Parentage:

*Female or seed parent.*—Unidentified proprietary seedling selection.

*Male or pollen parent.*—Unidentified proprietary seedling selection.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous daisy-type garden Chrysanthemum. Inverted triangle. Stems initially upright, then outwardly spreading giving a uniformly mounded appearance to the plant. Freely branching with lateral branches potentially developing at every node, when pinched, about 10 laterals develop.

*Plant height.*—About 23 cm.

*Plant spread.*—About 42 cm.

*Foliage description.*—Leaf arrangement: Alternate. Length: About 4.5 cm. Width: About 4.1 cm. Apex: Cuspidate to mucronate. Base: Truncate. Margin: Palmately lobed, sinuses parallel to divergent. Texture: Upper and lower surfaces moderately pubescent. Veins prominent on lower surface. Petiole length: About 1.9 cm. Petiole diameter: About 2 mm. Color: Young foliage upper surface: 147A. Young foliage lower surface: Close to 147B. Mature foliage upper surface: 147A. Mature foliage lower surface: 147B. Venation upper surface: 147A to 147B. Venation lower surface: 147B.

Inflorescence description:

*Appearance.*—Daisy-type inflroescence form with oblong-shaped ray florets. Inflorescences borne on terminals above foliage, arising from leaf axils. Disk and ray florets arranged acropetally on a capitulum. One inflorescence per terminal with numerous inflorescences per plant, about 10 to 12 per lateral stem.

*Flowering response.*—Under natural season conditions, plants flower in early October in the Northern Hemisphere, about 78 days after planting, and flower for at least three weeks depending on weather conditions.

*Inflorescence bud (before showing color).*—Height: About 5 mm. Diameter: About 7 mm. Phyllary color: Close to 141A.

*Inflorescence size.*—Diameter: About 4.1 cm. Depth (height): About 1.1 cm. Diameter of disc: About 1 cm.

*Ray florets.*—Shape: Oblong, concave. Length: About 1.9 cm. Width: About 5 mm. Apex: Dentate. Margin: Entire. Texture: Smooth, glabrous, satiny. Orientation: Initially upright, then horizontal. Number of ray florets per inflorescence: About 110. Color: When opening: Upper surface: Close to 70A. Lower surface: Slightly darker, but close to 69A. Opened infloresence: Upper surface: Close to 70B to 70C. Lower surface: Close to 69A.

*Disc florets.*—Shape: Tubular, apex dentate. Length: About 4 mm. Width: Apex: About 1 mm. Base: About 1 mm. Number of disc florets per inflorescence: Typically more than 100. Color: Immature: Close to 154A. Mature: Apex: 9A. Mid-section and base: Whitish green.

*Peduncle.*—Aspect: Flexible, angled about 35° to the stem. Length: First peduncle: About 5 cm. Fourth peduncle: About 6.6 cm. Diameter: About 1.5 mm. Texture: Pubescent. Color: Close to 144A.

*Reproductive organs.*—Androecium: Present on disc florets only. Anther color: 9A. Pollen: Scarce. Gynoecium: Present on both ray and disc florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named 'Empire Riviera', as illustrated and described.

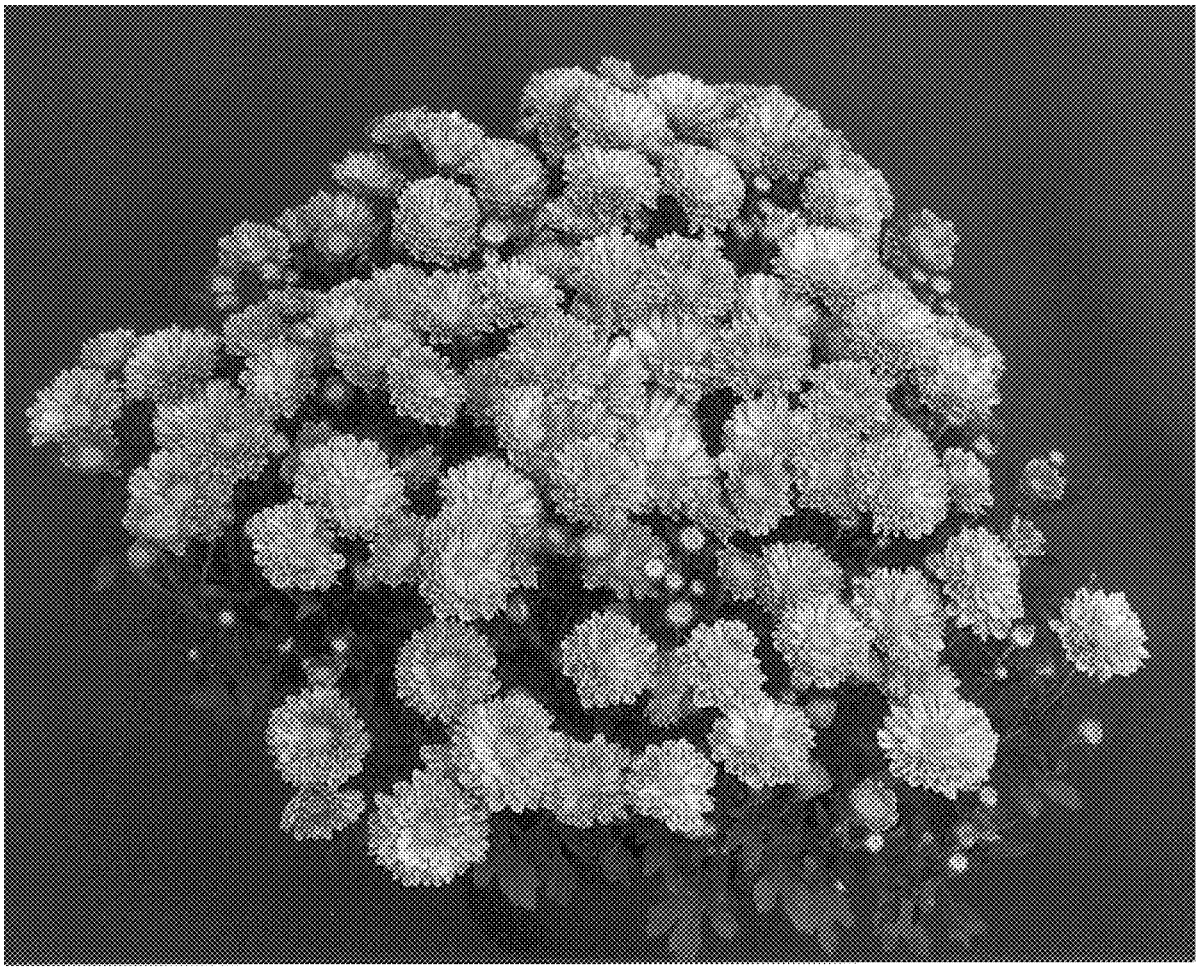
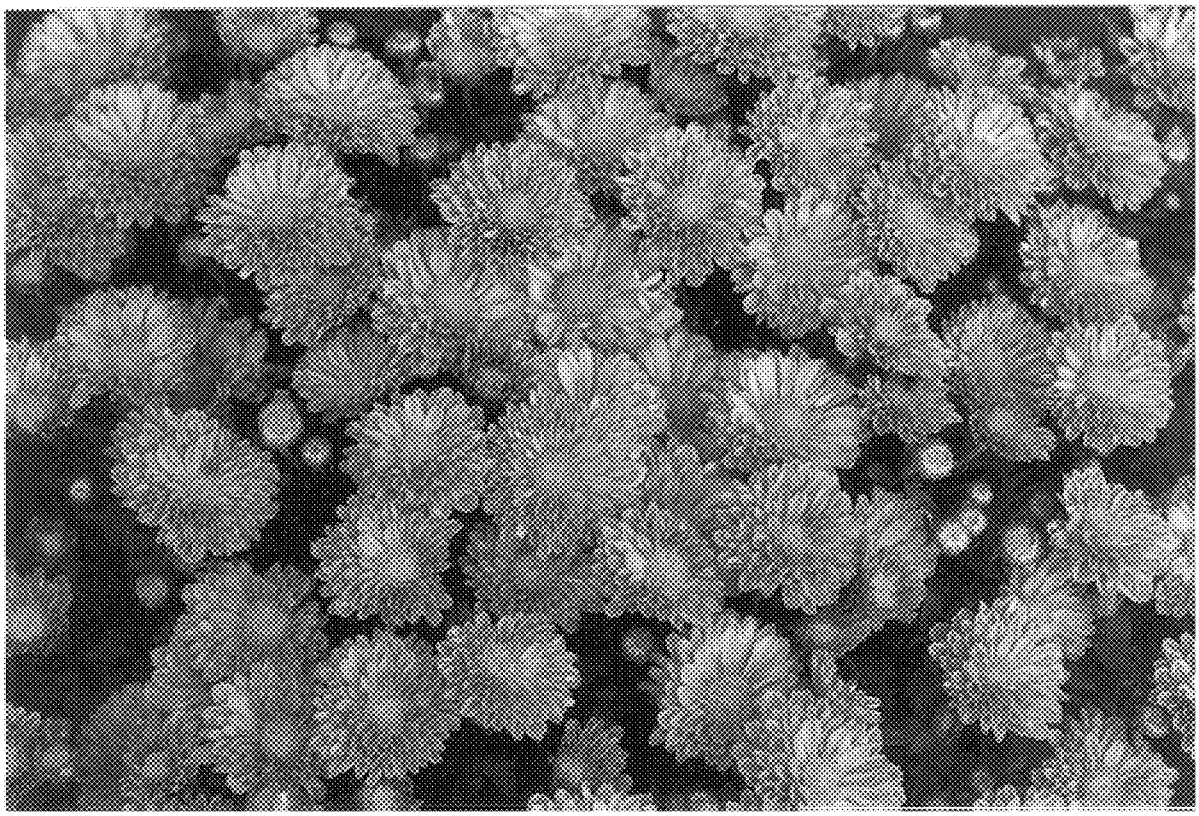

* * * * *